(12) United States Patent
Sprung

(10) Patent No.: US 7,945,306 B2
(45) Date of Patent: May 17, 2011

(54) METHOD FOR GENERATING AN IMAGE EXPOSURE OF THE HEART REQUIRING A PREPARATION

(75) Inventor: Katrin Christel Sprung, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 475 days.

(21) Appl. No.: 11/517,136

(22) Filed: Sep. 6, 2006

(65) Prior Publication Data

US 2007/0073138 A1 Mar. 29, 2007

(30) Foreign Application Priority Data

Sep. 9, 2005 (DE) .......................... 10 2005 043 024

(51) Int. Cl.
*A61B 5/05* (2006.01)

(52) U.S. Cl. ........ 600/413; 600/410; 600/407; 600/425; 600/437

(58) Field of Classification Search ........................ None
See application file for complete search history.

(56) References Cited

U.S. PATENT DOCUMENTS

| 5,000,182 | A | * | 3/1991 | Hinks | ........................... 600/413 |
| 5,239,591 | A | * | 8/1993 | Ranganath | ..................... 382/128 |
| 5,447,155 | A | * | 9/1995 | NessAiver et al. | ............ 600/410 |
| 6,262,575 | B1 | | 7/2001 | Bruder et al. | |
| 6,639,211 | B1 | | 10/2003 | Anand et al. | |
| 6,708,052 | B1 | * | 3/2004 | Mao et al. | ..................... 600/407 |
| 2002/0065459 | A1 | * | 5/2002 | MacAdam et al. | ........... 600/424 |
| 2003/0016851 | A1 | * | 1/2003 | Kaufman et al. | ............. 382/131 |

FOREIGN PATENT DOCUMENTS

WO WO 2004/008960 1/2004

\* cited by examiner

*Primary Examiner* — Unsu Jung
*Assistant Examiner* — Nigel Fontenot
(74) *Attorney, Agent, or Firm* — Schiff Hardin LLP

(57) ABSTRACT

A method for generation of an image exposure of the heart of an examination subject with an imaging medical examination apparatus in particular a magnetic resonance apparatus, the image exposure requiring preparation includes the steps of: preparation of the heart in a heart position that is relevant for the image acquisition and determination of the associated heart position, determination of at least one current heart position in the further course of the heart cycle, comparison of the determined current heart position with the heart position relevant for the image acquisition, and given correlation of the current heart position and the heart position relevant for the image acquisition, starting the image acquisition through a control device of the imaging medical examination apparatus.

19 Claims, 2 Drawing Sheets

A2

S2

A3

S3

A4

S4

METHOD FOR GENERATING AN IMAGE EXPOSURE OF THE HEART REQUIRING A PREPARATION

BACKGROUND OF THE INVENTION

1. Field of the Invention

The present invention concerns a method for creating an image exposure of the heart of an examination subject with an imaging medical examination apparatus, in particular a magnetic resonance apparatus, wherein the image exposure requires a preparation.

2. Description of the Prior Art

Often a preparation is necessary in order to generate heart image exposures should of a human or animal examination subject. For example, for what is known the "dark blood" technique, the signal of blood is suppressed and the surrounding tissue can be better detected, such that the heart muscle is better visible in the image representations. For this purpose, for example, preparation pulses for preparation of the actual measurement occurring in the end diastole are applied directly after the R-spike, which the highest positive amplitude of the electrocardiogram.

If the image data acquisition should occur in the end-diastolic phase, the person in charge of the image data acquisition (for example a medical-technical assistant, a doctor or a physician) must undertake a manual parameterization so that the image data are acquired at the desired time. The experience of the user is thereby decisive for the image quality since various possibilities for errors exist. For example, the measurement can be initiated at a point in time at which (given a slice acquisition) the prepared slice is not located in the same position as in the initial preparation, or the data acquisition can be initiated at a point in time at which the previously-saturated blood has already recovered again.

Such errors lead to limitations of the image quality, such that the acquired measurement possibly may not be usable and a repeat acquisition is required. Additional stresses thereby occur for the patient, for example if the image data acquisition must occur with a breath-hold or if breathing commands must be observed. The idle period in an examination apparatus (such as a scanner in magnetic resonance tomography) is extended and the system thus is blocked longer, with the result that subsequent examinations can be delayed. Errors due to an incorrect manual parameterization also cannot be completely precluded even when the operator (such as the technical assistants or doctors) I well-trained, such that the image quality is subject to significant fluctuations dependent on the person who happens to be the operator and anomalies in the patient and measurements must frequently be repeated.

SUMMARY OF THE INVENTION

An object of the invention is to provide a method for generation of an image exposure of the heart of an examination subject with an imaging medical examination apparatus (in particular a magnetic resonance apparatus), requiring image exposure preparation that is improved compared to the aforementioned problems.

The above object is achieved by a method including preparation of the heart in a heart position that is relevant for the image acquisition and determination of the associated heart position, determination of at least one current heart position in the further course of the heart cycle, comparison of the determined current heart position with the heart position relevant for the image acquisition and given correlation of the current heart position and the heart position relevant for the image acquisition, starting the image acquisition by a control device of the imaging medical examination apparatus.

According to the invention the heart position relevant for the preparation and therewith for the intended image exposure, is thus determined directly after the preparation of the heart. The position prepared for a later image exposure or an associated slice is therewith recognizably recorded.

In the further course of the heart cycle the heart phases (such as the contraction of the heart) are tracked and thus a series of current heart positions is determined.

The respectively-determined current heart positions serve as masks for the comparison with the heart position that is relevant for the image acquisition (which heart position was determined immediately after the preparation) and are compared with this.

Given a correlation of the immediately current heart position with the heart position that is relevant for the image acquisition, the start of the image acquisition is initiated by a control device of the imaging medical examination apparatus. Flawed exposures due to a too-early or too-late timing thus are effectively prevented via the corresponding automation of the acquisition. Time-intensive repeat acquisitions that are stressful for the patient are therewith dispensed with.

In a conventional method the user initially establishes a time value for the average heart cycle in milliseconds and this is, for example, entered into an acquisition protocol via a button press, and the user subsequently shifts the point in time for the actual image acquisition into the end diastole based on his or her own experience with the respective examination technique. In the inventive method, by contrast, no further parameterization is required after the establishment of the value for the average heart cycles. Rather, during the acquisition the measurement system according to the invention automatically establishes when the heart is in the position that is advantageous for the measurement and independently triggers the acquisition. In contrast to conventional procedures, is it apparent before the end of the image procedure whether the set value for the point in time of the image acquisition has led to a diagnostically-sufficient image quality. A repetition of image acquisitions because the image was measured at an incorrect point in time and thus because the acquired image or images are possibly not sufficiently useful is avoided with the inventive method.

According to the invention the image acquisition can be started entirely automatically or semi-automatically dependent on inputs of the operator via the control device. In the case of a fully automatic start of the image acquisition, a determination of the current heart position at specific time intervals is implemented (for example by a program of the control device) and the image acquisition is started after a subsequent, fully automatic image comparison, with parameters being used that are suitable for the respective acquisition technique. The program can additionally take into account patient-specific information, for example about existing or presumed illnesses. If applicable an access to databanks or knowledge-based systems can be used for this.

Furthermore, the image acquisition can be started semi-automatically by additional inputs of an operator (such as a technical or doctor) being taken into account. For example, a manual parameter input can be processed and evaluated by the program of the control device or supplementary information that the operator inputs for the heart cycle of the patient or the patient's illnesses can be used for the image acquisition start. In each case no purely-manual image acquisition occurs, such that problems due to a false timing of the measurement can be largely avoided.

The heart position relevant for the image acquisition and/or the current heart position can be determined by generation of image exposures, in particular in the framework of short measurements, possibly with assistance by the generation of an electrocardiogram. The heart phases can be actively tracked using the electrocardiogram, or repeated short measurements for image data that are normally used in combination. For example, image exposures can be generated at predetermined time intervals and compared with the first image acquisition for the relevant heart position in the preparation. For better assessment of the image exposures, an electrocardiogram can additionally be used that provides further information about the respective heart phase. For example, the R-spike is to with the end diastole.

The heart position that is relevant for the image acquisition and/or the current heart position can be determined automatically by a previous parameterization. It is thus possible for the data acquisition to be automatically initiated in the form of short measurements for determination of the current heart position, or this can ensue essentially automatically, but an operator can alter such a protocol for automatic determination of current heart positions by preceding inputs, for example in order to obtain a higher density of the short measurements in the time response.

The relevant or current heart position can additionally be determined by a prior parameterization, whereby a user either actively triggers short acquisitions or actively inputs associated times or time spans beforehand. The determination of the heart positions on the basis of a preceding parameterization can be supported by specific acquisition protocols being provided that procedure (by corresponding parameters) a minimum standard for the determination of the positions, such that the parameterization on the part of the user is limited in this sense by specifications. If the comparison of the current heart position with the relevant heart position is positive for the image exposure, a correlation thus exists; the actual image acquisition is subsequently started entirely automatically or semi-automatically.

For the determination of the heart positions, and in the image acquisition slice images can be generated and, in the comparison of the heart positions, the correlation with the respective slice can be checked. For example, for acquisition by magnetic resonance tomography, slices of some millimeters thickness are acquired. A typical slice thickness is, for example, 8 mm, thus in a range of approximately 10 mm. If the heart positions are now compared, the correlation to the respective slice is checked since the heart position relevant for the image acquisition identifies the slice that should be measured in the framework of the provided image acquisition (for example in the end diastole).

According to the invention, the program can compare the determined current heart position with the heart position relevant for the image acquisition, in particular a program implemented on the control device. For this purpose, the program can possibly receive inputs of an operator, for example with regard to the criteria that are to be applied for establishment of a correlation. Furthermore, the operator can assign various algorithms to the program to which this should resort. For this, different comparison protocols or types are appropriately provided for selection via a user interface, the selection of which depends, for example, on how thoroughly (accurately) the comparison is to be implemented, or how critical a small deviation of the acquisition position from the desired acquisition position is for the respective image acquisition. For comparison the program can resort to methods of image recognition and processing or also to methods for edge detection and evaluation for processing of the signals of the electrocardiogram.

An image subtraction and/or an image superimposition and/or a detection of edges and/or structures can be implemented in the framework of the comparison of the determined current heart position with the heart position relevant for the image acquisition, possibly using information of a medical databank. A high correlation can be detected by means of an image subtraction since only very little image information exists in the remaining subtraction image. An image superimposition can additionally be implemented in order to check the extent to which two images are congruent. The comparison also can be by edge detection or a detection of typical structures in a given anatomical region by, for example, comparing the detected edges associated with anatomical structures (if applicable after determination of their spatial position) according to their position in the various exposures of the heart positions.

Information of a medical databank can be accessed for this purpose, which databank contains, for example, a series of typical image exposures of this or another patient, or information regarding how a subtraction image is to be viewed so that the position is correctly selected for the following image exposure. The comparison thus can be adaptively implemented using learning systems (neural networks), such that by degrees a better determination of the correct point in time for the image acquisition is possible. If applicable, extended assessments by an operator who evaluates the produced image quality can be provided for this.

The current heart position can be determined at intervals of 10 ms to 200 ms, in particular every 50 ms or every 100 ms. Naturally other intervals can be selected if applicable. It is also possible that the intervals between the individual short measurements are not constant but rather initially exhibit, for example, larger intervals. By moving the point in time presumably suitable for the image acquisition, closer measurements are conducted more often, possibly every millisecond or more frequently or at least every 10 ms. Sufficiently fast slice correlations or the like are thereby checked by superimposition of the edges or comparison of at least one part of the image data. The comparison of the respective current heart position must be started during the measurement or be implemented in a timely manner afterwards, such that the image acquisition can be started promptly if applicable. Here only a reduced image data set of the short measurements can normally be evaluated, or the data acquisition is directly limited depending on the computer capacity that is available for the comparison.

The correlation of the current heart position and the heart position relevant for the image acquisition can be determined with an allowable deviation. The desired image quality for the concluding image acquisition can be established by the specification of such a deviation in a program or additionally via an operator input. It is thereby taken into account that the current heart position in the framework of the interval measurements normally will not precisely correspond to the original position determined as a relevant heart position. Nevertheless, a correlation with a specific error range can by all means be sufficient in order to ensure an image acquisition with a good quality. For example, in the case of an image subtraction the edges can not disappear entirely but rather disappear at, for example, 98% (depending on the allowable deviation). In the context of an allowable deviation of 2% or 3% (input, for example, by an operator), the final measurement can then be initiated nevertheless, which final measurement leads to image exposures that enable a safe diagnosis generation. An allowable deviation can adopt significantly different values with the type of the image exposures to be generated and their diagnostic importance and the like.

A dark blood exposure or a different exposure can be generated in the end diastole of the heart. Given acquisition in the dark blood technique the signal of the blood is thereby suppressed by preparation pulses, so the heart muscle can be detected better.

Furthermore, other image acquisitions can be used that must be implemented in a specific phase of the heart (which can also deviate from the end-diastolic phase) after a preceding preparation, such that a relevant heart position (that, in the broadest sense, is understood as a preparation for a subsequent image acquisition) is provided.

Preparation pulses can be applied in the framework of the preparation. For example, given the image acquisition with a magnetic resonance apparatus radio-frequency pulses effect a saturation of the blood such that the signal of the blood is suppressed in the image exposures. The measurement is thereby prepared, for example in the dark blood technique. Other preparation methods can alternatively or additionally be used via which the slice or heart position relevant for the image acquisitions is likewise provided.

Moreover, the invention concerns an imaging medical examination apparatus that is fashioned for implementation of the method described above. This imaging medical examination apparatus includes an arrangement to determine the relevant heart position after a preparation and to subsequently track the heart cycle, so a current heart position is determined at least once. A computer compares the current heart position with the heart position relevant for the image acquisition, for which purpose a program is suitable that is accessible via a control device of the imaging medical examination apparatus. Given a correlation of the positions, the control device initiates the beginning of the image acquisition.

DESCRIPTION OF THE PREFERRED EMBODIMENTS

Figure 1A:
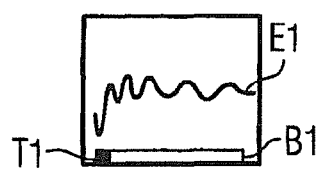
FIGS. 1A and 1B respectively show an electrocardiogram with a time bar and an associated heart image of the heart position relevant for the image acquisition.

FIG. 1A shows an electrocardiogram E1 with a time bar B1. In the time bar B1 a point in time T1 is marked relatively early in the representation, at which point in time T1 an image acquisition is established directly following a preparation. An image data acquisition at the marked point in time T1 leads to the heart image of the image exposure A1 shown in FIG. 1B, from which the heart position relevant for the actual image acquisition is determined. The actual image acquisition with the imaging medical examination apparatus is to be implemented later at this heart position of FIG. 1B.

In the further course of the heart cycle the current heart position is determined from time to time via the electrocardiogram with the aid of the controller.

Figure 1B:
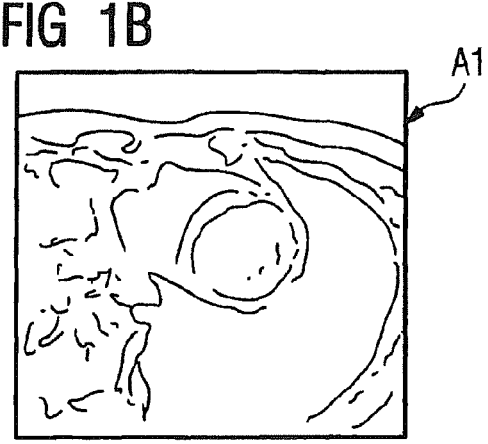
Figure 2A:
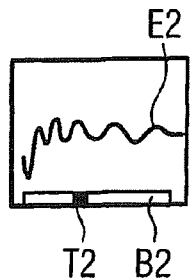
FIGS. 2A and 2B respectively show an electrocardiogram with a time bar and associated heart image of a current heart position.
Figure 2B:

In FIG. 2A an electrocardiogram E2 is shown below which a time bar B2 is shown in which a point in time T2 is marked that, in comparison to the point in time T1 of the time bar B1, is to be associated with a later point in time in the heart cycle. A current heart position is determined via a short measurement at this later point in time T2, so that an image exposure A2 results as is shown in FIG. 2B. From the image exposure A2 at the point in time T2 a current position of the heart is determined for comparison with a heart position relevant for the concluding image acquisition, this relevant heart position being provided by the image exposure A1 of FIG. 1B.

Figure 2C:
FIG. 2C is a subtraction image of the relevant heart position according to FIG. 1B and the current heart position according FIG. 2B.

For comparison of the heart positions of FIGS. 1B and 2B an image subtraction is implemented, the result of which is shown in FIG. 2C. Edges are still clearly detectable in the subtraction image 2C, allowing a suitable program to acquire the information that the identical heart position has not yet been reached and the actual image acquisition thus can not yet be started.

Figure 3A:
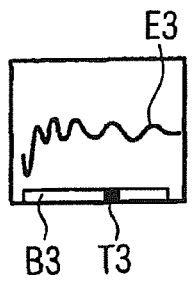
FIGS. 3A and 3B respectively show an electrocardiogram with a time bar and associated heart image of a further current heart position.
Figure 3B:
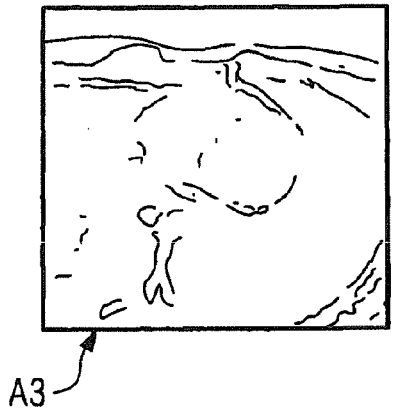
Figure 3C:
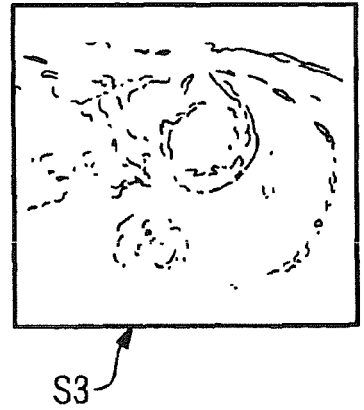
FIG. 3C is a subtraction image of the relevant heart position according to FIG. 1B and the current heart position according FIG. 3B.

In the further course of the heart cycle, a short measurement that shows a further current heart position (as is shown in FIG. 3B) is produced at a later point in time T3 (as shown in FIG. 3A), some 10 ms later. The heart position is established by the electrocardiogram E3 with the time bar B3 as well as the image data determined via the short measurement. The subtraction image between the image exposure A3 of FIG. 3B and the exposure A1 of FIG. 1B is shown in FIG. 3C. Like the subtraction image S2, here as well the subtraction image S3 still contains a plurality of image data, but a decrease (attenuation) of the edges is recognizable in regions. Nevertheless, the remaining edges of the subtraction image S3 show that there still exists no correlation of the relevant heart position with the current heart position.

Figure 4A:
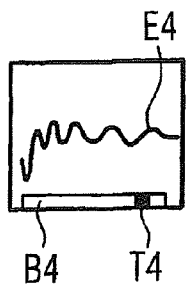
FIGS. 4A and 4B respectively show an electrocardiogram with a time bar and an associated heart image of a further, later current heart position.
Figure 4B:
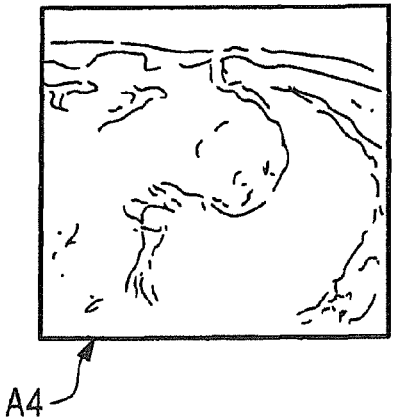
Figure 4C:
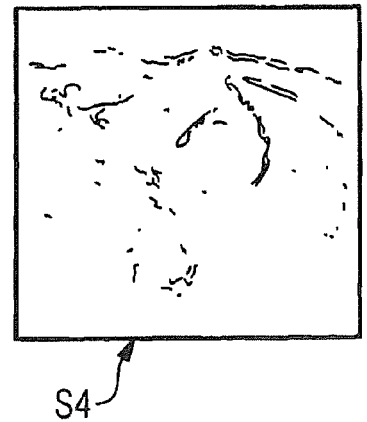
FIG. 4C is a subtraction image of the relevant heart position according to FIG. 1B and the current heart position according FIG. 4B.

Furthermore, after the expiration of a specific time interval a short measurement (with the result shown in FIG. 4B) is produced again at the point in time T4 (as shown in FIG. 4A) using the electrocardiogram E4. An image subtraction is also produced for image exposure A4 of FIG. 4B, with databank information being accessed for evaluation of remaining edges. The subtraction image S4 is shown in FIG. 4C. The edges are clearly weaker than those in the earlier subtraction images S2 and S3.

Nevertheless, the deviation is still too much to allow the assumption of a sufficiently-identical heart position. An image exposure (not shown here) is now generated, and given a sufficient disappearance of the edges of the associated subtraction image, the original heart position is achieved exactly (within the limits of an allowable deviation), whereupon the final measurement is initiated. Errors due to an incorrect positioning of the heart in an image acquisition are thereby reliably avoided by the inventive method, so repeat exposures with associated stresses for the patient can be avoided.

Figure 5:
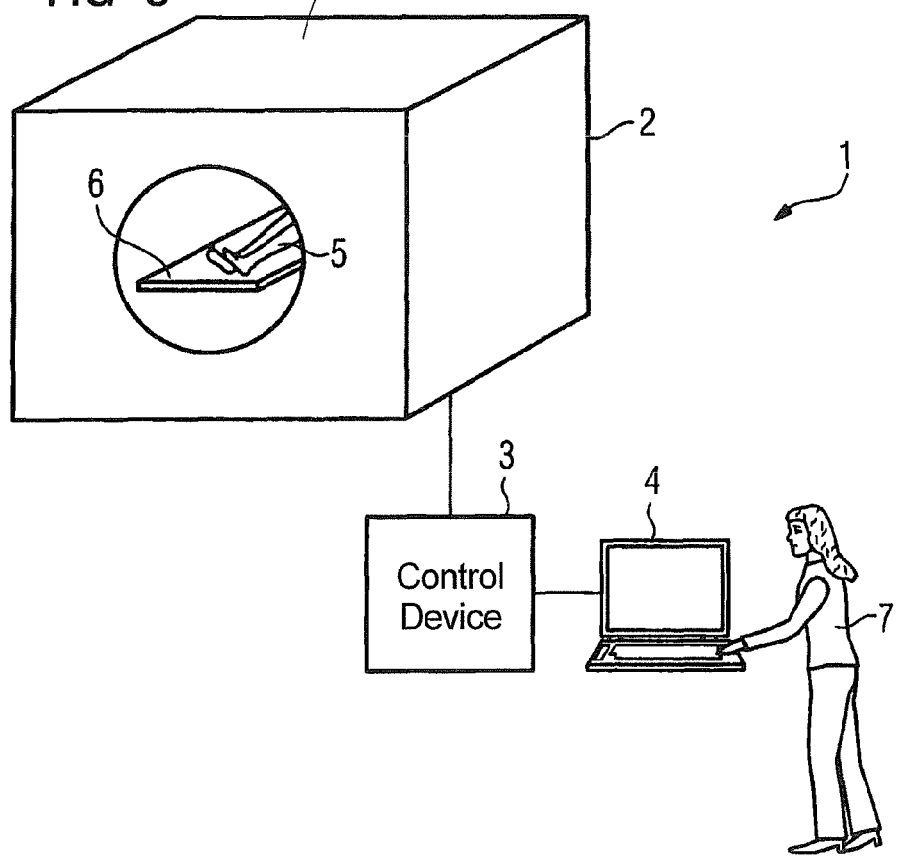
FIG. 5 schematically shows an inventive imaging medical examination apparatus.

FIG. 5 shows an imaging medical examination apparatus 1 that implements the above-described method. The apparatus 1 has an image acquisition device 2 as well as a control device 3 and an associated image output unit 4. A patient 5 lying on a patient table 6 is inserted into the acquisition device 2. After preparation of the heart of the patient 5, an image exposure is generated (with simultaneous generation of an electrocardiogram) with the acquisition device 2 as a slice image that determines the heart position relevant for an actual later image acquisition.

In the further course of the heart cycle of the patient 5, short measurements are conducted with the acquisition device 2 at specific time intervals, from which short measurements the further current heart positions can be acquired. The acquisition of these short measurements is controlled by the control device 3 of the imaging medical examination apparatus 1. Furthermore, an access to a program is possible through the control device 3, the program conducting a comparison of the respectively-determined current heart position with the heart position relevant for the image acquisition.

The output unit 4 in the form of a monitor is provided with an input device via which an operator 7 can make inputs in order to influence the determination of the current heart position and the current image acquisition by specifications (such as parameters) in advance. Dependent on these specifications of the operator 7, the image acquisition is automatically started by the control device 3 given a correlation between the relevant heart position with the immediately current heart position (within the limits of an allowable deviation). The comparison of the heart positions ensues using image processing and evaluation techniques such as an image subtraction as well as edge detection and the like. The control device 3 can access databank systems (not shown here) for this purpose.

By the automatic triggering of the image acquisition it is ensured that the measurement is initiated at a point in time at which the prepared slice is located in a position identical to that in the initial preparation for the generation of slice exposures with the acquisition device 2. This occurs in a timely manner as long as the preparation effect is still present. Repeat exposures are therewith avoided and the wait times for patients in the acquisition device 2 are kept short.

Although modifications and changes may be suggested by those skilled in the art, it is the intention of the inventor to embody within the patent warranted hereon all changes and modifications as reasonably and properly come within the scope of her contribution to the art.

I claim as my invention:

1. A method for generating an image exposure of a heart, said image exposure being acquired with a medical imaging apparatus using an image exposure protocol that gives said image exposure a diagnostically-sufficient image quality, said method comprising the steps of:
    acquiring a first image comprising a depiction of the heart in a heart position, within cardiac cycle, that is relevant for said image exposure, by operating said medical imaging apparatus with a different imaging protocol from said image exposure imaging protocol;
    acquiring a plurality of second images, each at a different time within the cardiac cycle, also by operating said medical imaging apparatus with said different imaging protocol, each comprising a depiction of the heart in a different current position at a different time within the cardiac cycle;
    in a control unit of the medical imaging apparatus, automatically determining when substantial depiction correlation exists between the current position depicted in one of said second images and the position of the heart depicted in said first image; and
    when said substantial depiction correlation is determined to exist, triggering, from said control unit, operation of said medical imaging apparatus to acquire said image exposure with said image exposure protocol.

2. The method as claimed in claim 1 comprising starting said image exposure acquisition completely automatically through said control unit.

3. The method as claimed in claim 1 comprising starting said image exposure acquisition semi-automatically through said control unit, dependent on an input manually entered into said control unit.

4. The method as claimed in claim 1 comprising automatically, without manual intervention, determining at least one of said heart position relevant for the image exposure acquisition and the current heart position.

5. The method as claimed in claim 1 comprising determining at least one of the heart position relevant for the image exposure acquisition and the current heart position based on a parameterization entered into said control unit.

6. The method as claimed in claim 1 comprising the first image acquisition as a first slice image, and determining said current heart position as second slice images image, and determining said substantial correlation of the current heart position and the heart position relevant for the image exposure acquisition by comparing said first slice image and said second slice images in said control unit image.

7. The method as claimed in claim 1 comprising determining said substantial correlation of the current heart position and the heart position relevant for the image acquisition by executing a computer program in said control unit.

8. The method as claimed in claim 1 comprising determining said substantial correlation by superimposition of said first image with each of said second image.

9. The method as claimed in claim 1 comprising determining said substantial correlation by detection of image features, selected from the group consisting of edges and anatomical structures in each of the first image and each of the second image, and comparing the respective image features detected in the first image and in the second image.

10. The method as claimed in claim 1 comprising acquiring said second images at intervals in a range between 10 ms and 200 ms.

11. The method as claimed in claim 1 comprising acquiring said second images every 50 ms.

12. The method as claimed in claim 1 comprising acquiring said second images every 100 ms.

13. The method as claimed in claim 1 comprising determining said substantial correlation within a predetermined deviation from exact correlation.

14. The method as claimed in claim 1 comprising operating said medical imaging apparatus to acquire a dark blood exposure image of the heart at an end of diastole in the cardiac cycle as said image exposure.

15. The method as claimed in claim 1 wherein said medical imaging apparatus is a magnetic resonance imaging apparatus, and comprising preparing the heart for said image exposure by generating preparation pulses with said magnetic resonance imaging apparatus.

16. The method as claimed in claim 1 comprising employing, as said different imaging protocol, an imaging protocol that has a shorter acquisition time than said image exposure imaging protocol.

17. The method as claimed in claim 16 comprising obtaining an electrocardiogram of examination subject and executing said short image acquisition measurements at respective times designated within the electrocardiogram.

18. A medical imaging system for generating an image exposure of a heart, said image exposure being acquired using an image exposure protocol that gives said image exposure a diagnostically-sufficient image quality, comprising:

a medical imaging apparatus configured to be operated with a different imaging protocol from said image exposure imaging protocol to acquire a first image comprising a depiction of the heart in a heart position, within cardiac cycle, that is relevant for said image exposure;

said medical imaging apparatus also being configured to be operated with said different imaging protocol to acquire a plurality of second images, each comprising a depiction of the heart in a different current position within the cardiac cycle;

a control unit configured to automatically determine when substantial depiction correlation exists between the current position depicted in one of said second images and the position of the heart depicted in said first image; and said control unit, when said substantial depiction correlation is determined to exist, being configured to trigger operation of said medical imaging apparatus to acquire said image exposure with said image exposure protocol.

19. The medical imaging system as claimed in claim 18 wherein said medical imaging apparatus is a magnetic resonance data acquisition unit, and wherein said control unit is configured to operate said magnetic resonance imaging data acquisition unit to prepare the heart for an image acquisition by causing said magnetic resonance data acquisition unit to generate preparation pulses.

* * * * *